United States Patent [19]

Brownstein

[11] Patent Number: 4,675,416
[45] Date of Patent: Jun. 23, 1987

[54] TERNARY CHARGE TRANSFER COMPLEX

[75] Inventor: Sydney K. Brownstein, Ottawa, Canada

[73] Assignee: Canadian Patents and Development Limited-Societe Canadienne des Brevets et d'Exploitation Limitee, Ottawa, Canada

[21] Appl. No.: 752,082

[22] Filed: Jul. 3, 1985

[30] Foreign Application Priority Data

Jul. 11, 1984 [CA] Canada .................................. 458579

[51] Int. Cl.$^4$ ...................... C07D 327/00; C07F 5/06; C07F 9/90; C07F 15/02
[52] U.S. Cl. ........................................... 549/3; 549/4; 556/1; 556/42; 556/51; 556/57; 556/64; 556/69; 556/81; 556/85; 556/138; 556/139; 556/177; 556/180; 548/101; 548/102; 548/110; 568/1
[58] Field of Search ............... 568/1; 556/1, 177, 180, 556/64, 69, 138, 139, 85, 81, 51, 42, 57; 548/101, 102, 110; 549/3, 4

[56] References Cited

U.S. PATENT DOCUMENTS

| | | | |
|---|---|---|---|
| 1,944,274 | 1/1934 | Salzberg | 556/42 X |
| 2,749,213 | 6/1956 | Bruce | 556/81 X |
| 3,542,828 | 11/1970 | Harris | 556/64 |
| 3,663,450 | 5/1972 | Cozewith et al. | 556/51 X |
| 4,388,227 | 6/1983 | Kalnin | 556/177 X |

OTHER PUBLICATIONS

Thomas, Anhydrous Aluminum Chloride, Reinhold Publ. Corp. N.Y. pp. 157 & 158 (1941).
Chemical Abstracts vol. 82, 86357z (1975).
Chemical Abstracts vol. 102; 124482c (1985).
Chemical Abstracts vol. 76,92338m & 92345m (1972).
Chemical Abstracts vol. 74,8288y (1971).

Primary Examiner—Helen M. S. Sneed
Attorney, Agent, or Firm—Wenderoth, Lind & Ponack

[57] ABSTRACT

Disclosed herein are organometallic ternary charge transfer complexes of the formula (I)

$$a(RX) \cdot MX \cdot b(Ar) \qquad (I)$$

wherein
RX is an inorganic chloride or fluoride which contains at least one oxygen and/or sulfur atom and is capable of forming a complex salt $a(R) \cdot MX_{(a+m)}$ with the Lewis acid $MX_m$, such as NOCl or NOF, $MX_m$ is a Lewis acid metal chloride or fluoride, such as $BCl_3$, $BF_3$, $AlCl_3$, $GaCl_3$, $TlCl_3$, $AsCl_3$, $AsF_5$, $SbCl_5$, $FeCl_3$, $SnCl_4$, $TiCl_4$, $ZrCl_4$, $NbCl_5$, $TaCl_5$, $MoCl_5$ and $WCl_6$, Ar is an aromatic compound, such as napthalene, anthracene, thiophene, furan and benzene which is unsubstituted or substituted with lower alkyl, halogen, diloweralkylamino, oxo or lower alkoxy, m is an integer representing the valency of the metal M, a is an integer selected such that the sum of a and m does not exceed the coordination number of the metal M of the given valency, b is 0.5, 1 or 2

The inorganic chlorides or fluorides RX are typically NOCl, $SOCl_2$ or NOF. The complexes of formula (I) are intensely colored solids, mostly stable to dissociation. They are reasonably conducting, thus are useful as organic conductors, and being intensely colored, are valuable as dyes and coloring materials.

13 Claims, No Drawings

TERNARY CHARGE TRANSFER COMPLEX

The present invention relates to a novel organometallic ternary charge transfer complex, to a process for producing the same and to an electrically conductive material which contains the same as a conductor.

The first demonstration of what are now called charge transfer compounds were iodine/aromatic complexes where equilibrium constants of 1 and 6 were found for benzene and mesitylene (cf. H. A. Benesi et al, J. Am. Chem. Soc. 1949, 71, 2703-2707). A characteristic of these complexes is the large shift in ultraviolet absorption, which was explained by the partial transfer of a $\pi$ electron from the donor to the acceptor species (cf. R. S. Mulliken, J. Am. Chem. Soc. 1952, 74, 811-824). Particularly strong complexes were found with tetracyanoethylene as acceptor giving equilibrium constants of 2 for benzene and 17 for mesitylene (cf. R. E. Merrifield, J. Am. Chem. Soc. 1958, 80, 2778-2782). Even stronger charge transfer complexes from better donors and acceptors have conductivities approaching those of normal metals and some even exhibit superconductivity (cf. J. O. Williams, Adv. Phys. Org. Chem. 1978, 16, 159-237 and M. R. Bryce et al, Nature 1984, 309, 119-126). The range of conductivities is from about $10^{-20}$ ohm$^{-1}$ cm$^{-1}$ for a typical organic crystal to $10^3$ ohm$^{-1}$ cm$^{-1}$ for complexes of tetracyanoquinodimethane with good donors such as tetramethyltetraselenofulvalene.

One disadvantage of the charge transfer complexes hitherto known is that the starting materials for them are expensive. For example, tetracyanoethylene, tetracyanoquinodimethane and tetramethyltetraselenofulvalene are all very expensive and so accordingly charge transfer complexes resulting from these raw materials are also very expensive. Thus it has been desired that charge transfer complexes with a certain degree of conductivity are prepared from relatively cheap raw materials so that the resulting charge transfer complexes may be adopted extensively in commercial use.

It has now been found that Lewis acid metal chlorides or fluorides, when used with certain inorganic chlorides or fluorides, form stable organometallic charge transfer complexes which have a certain conductivity and are useful as electrical conductors.

One aspect of the present invention provides an organometallic ternary charge transfer complex of formula (I)

$$a(RX).MX_m.b(Ar) \qquad (I)$$

wherein
- $MX_m$ is a Lewis acid metal chloride or fluoride,
- RX is an inorganic chloride or fluoride which contains at least one oxygen and/or sulfur atom and is capable of forming a complex salt $a(R).MX_{(a+m)}$ with the Lewis acid $MX_m$,
- Ar is an aromatic compound with the proviso that unsubstituted benzene is excluded when $MX_m$ is $BCl_3$, $BF_3$, $SnCl_4$, $TiCl_4$, $ZrCl_4$, $AsCl_3$ or $AsF_5$
- m is an integer representing the valency of the metal M,
- a is an integer selected such that the sum of a and m does not exceed the coordination number of the metal M of the given valency, and
- b is 0.5, 1 or 2.

Another aspect of the present invention provides a method for producing the ternary charge transfer complex of formula (I) as defined above, which method comprises admixing the inorganic chloride or fluoride, RX, a Lewis acid metal chloride or fluoride $MX_m$ and an aromatic compound Ar.

Still another aspect of the present invention provides an electrically conductive material which contains as a conductor the ternary charge transfer complex as defined above.

In formula (I), the inorganic chloride or fluoride, RX may be a non-metallic inorganic chloride or fluoride containing at least one oxygen atom or sulfur atom or both and may further contain a non-metallic atom of Group IV or V of the Periodic Table. Examples of these inorganic chlorides or fluorides include NOCl, $SOCl_2$, $NO_2Cl$, $COCl_2$, $(NSCl)_3$, NOF and $SCl_4$. Preferred inorganic chlorides are NOCl, $SOCl_2$ and NOF, particularly NOCl.

The metal M in the Lewis acid metal chloride $MX_m$ can be for example, B, Al, Ga, Tl, As, Sb, Fe, Sn, Ti, V, Nb, Ta, Mo, W, Th, U, Ni or Zr or a rare earth metal, and the metal halide $MX_m$ can be, for example, $BCl_3$, $BF_3$, $AlCl_3$, $GaCl_3$, $AsCl_3$, $AsF_5$, $SbCl_5$, $FeCl_3$, $SnCl_4$, $TiCl_4$, $ZrCl_4$, $VCl_3$, $NbCl_5$, $TaCl_5$, $TlCl_3$, $MoCl_5$, $WCl_6$, $UCl_6$, $ThCl_4$, a rare earth metal chloride such as $LaCl_3$, or $ZnCl_2$. Preferred metal halides, because they form a strong complex, are $AlCl_3$, $FeCl_3$, $AsF_5$ and $SbCl_5$.

The aromatic compounds Ar can be any aromatics which do not have one or more substituents which interfere with the formation of the charge transfer complex. The hydroxy, carboxy, amino, monosubstituted amino and sulfo groups will perhaps interfere with the complex formation. The aromatics include, for example, benzene which is unsubstituted or substituted with lower alkyl, halogen, diloweralkylamino, oxo or loweralkoxy; naphthalene; anthracene; polycondensed aromatic hydrocarbons; thiophene; furan; N-substituted pyrroles; porphyrins; and polystyrene. Aromatic compounds which have one or more electron donating groups, such as loweralkyl groups (e.g. methyl, ethyl), loweralkoxy groups (e.g. methoxy), diloweralkylamino groups (e.g. dimethylamino) and halogens (e.g. chlorine, bromine, iodine) are preferred. Particularly preferred are thiophene, furan and benzene derivatives which contain 1 to 6 methyl groups thereon, for example, toluene, p-xylene, mesitylene (1,3,5-trimethylbenzene) and hexamethylbenzene. It seems that thiophene, furan and hexamethylbenzene are very strong complex formers.

The integer a is selected such that the sum of a and m does not exceed the coordination number of the metal M of the given valency. For example, when $AlCl_3$ and NOCl are chosen as the metal chloride and the oxychloride, respectively, a is 1 because the coordination number of aluminum ($Al^{3+}$) is 4 and m is 3. When $TiCl_4$ and NOCl are chosen, a is 2 because the coordination number of titanium ($Ti^{4+}$) is 6 and m is 4. The preferred value for a is 1.

The number b can be 0.5, 1 or 2. However it is preferred that b multiplied by (the number of aromatic rings in the aromatic compound Ar) is equal to a. For example, when NOCl, $AlCl_3$ and naphthalene are employed, a is 1 in accordance with the above criterion. Naphthalene has two aromatic rings and a preferred value for b is 0.5. When two mols of NOCl per mol of $TiCl_4$ are employed, and hexamethylbenzene which has only one aromatic ring is employed as the aromatic compound, a preferred value for b is 2. When naphthalene is employed in place of hexamethylbenzene, a preferred value for b is 1.

The following Table 1 includes representatives of the organometallic ternary change transfer complexes of the present invention with certain characteristic properties.

The complexes referred to in Table 1 were made by methods analogous to those in Examples 1 and 2 below.

TABLE 1

| Complex | Absorption ($\lambda$ max Å) | Chemical Shift ($\delta^1$H, $\delta^{13}$C) | | Conductivity (ohm$^{-1}$ cm$^{-1}$) |
|---|---|---|---|---|
| NOCl.AlCl$_3$.Benzene | 3350 | 8.03 | 137.1 | |
| NOCl.AlCl$_3$.Toluene | 3380 | 2.67 | | |
| | | 7.92 | | |
| NOCl.AlCl$_3$.p-Xylene | 3400 | 2.63 | 139.9 | |
| | | 7.81 | | |
| NOCl.AlCl$_3$.Mesitylene | 3430 | 2.58 | | |
| | | 7.58 | | |
| | | | 17.3 | |
| NOCl.AlCl$_3$.Hexamethylbenzene | 3340 | 2.48 | 149.9 | |
| NOCl.AlCl$_3$.0.5 Naphthalene | 3950 | | 133.39 | |
| | | | 135.37 | |
| NOCl.AlCl$_3$.Anthracene | 4520 | | | |
| NOCl.AlCl$_3$.Polystyrene | Brown | | | |
| NOCl.AlCl$_3$.p-Dichorobenzene | Brown | | | |
| NOCl.AlCl$_3$.Bromobenzene | Red | | | |
| NOCl.AlCl$_3$.o-Diiodobenzene | Brown | | | |
| NOCl.AlCl$_3$.p-Benzoquinone | Colored | | | |
| NOCl.AlCl$_3$.Thiophene | Black | | | |
| NOF.BF$_3$.Toluene | Colored | | | |
| NOCl.BCl$_3$.Toluene | Colored | | | |
| NOF.BF$_3$.p-Xylene | Colored | 2.25 | | |
| | | 7.05 | | |
| NOCl.BCl$_3$.p-Xylene | Colored | | | |
| NOF.BF$_3$.Mesitylene | Colored | 2.29 | | |
| | | 6.93 | | |
| NOCl.BCl$_3$.Hexamethylbenzene | Colored | | | |
| NOF.BF$_3$.Hexamethylbenzene | 3250, 2700 | 2.42 | | |
| NOCl.GaCl$_3$.Benzene | 3350 | 7.76 | 134.8 | |
| NOF.BF$_3$.Naphthalene | Black | | | |
| NOCl.GaCl$_3$.0.5 Naphthalene | 4950 | | | |
| NOCl.GaCl$_3$.Chlorobenzene | 2900 | 7.38 | | |
| NOCl.TiCl$_3$.Benzene | Colored | 7.60 | 132.2 | |
| NOF.BF$_3$.Anthracene | Colored | | | |
| NOCl.AsCl$_3$.Toluene | Colored | | | |
| NOF.AsF$_5$.Hexamethylbenzene | 3340, 2700 | 2.39 | | 1.36 × 10$^{-7}$ Crystal Structure |
| NOCl.AsCl$_3$.Hexamethylbenzene | Colored | | | |
| NOCl.AsCl$_3$.N,N—dimethylaniline | Colored | | | |
| NOCl.SbCl$_5$.Benzene | 3440 | 7.81 | 136.7 | |
| NOCl.SbCl$_5$.2 Toluene | 3400 | 2.70, 7.97, 8.05 | | Crystal structure |
| NOCl.SbCl$_5$.Hexamethylbenzene | 3340 | 2.47 | 18.2, 150.2 | 2.3 × 10$^{-3}$ Crystal Structure |
| NOCl.SbCl$_5$.t-Butylbenzene | 3390 | 7.87, 7.96, 8.05 | 30.5, 36.5, 134.3, 134.8, | |
| NOCl.SbCl$_5$.Naphthalene | Colored | | | |
| NOCl.SbCl$_5$.p-Xylene | 3400 | 2.63, 7.81 | 136.9, 163.5 20.8, 137.8, 148.0 | |
| NOCl.SbCl$_5$.Thiophene | Colored | | | 3.0 × 10$^{-6}$ |
| NOCl.SbCl$_5$.N,N—Dimethylaniline | Colored | | | 1.9 × 10$^{-10}$ |
| NOCl.SbCl$_5$.Polystyrene | Colored | | | 1.6 × 10$^{-2}$ |
| NOCl.FeCl$_3$.Benzene | 3475 | | | |
| NOCl.FeCl$_3$.Hexamethylbenzene | 3610 | | | |
| NOCl.FeCl$_3$.Naphthalene | Colored | | | |
| NOCl.FeCl$_3$.Anthracene | Colored | | | |
| 2NOCl.SnCl$_4$.t-Bu—benzene | 3600 | | | |
| 2NOCl.SnCl$_4$.p-Xylene | Colored | 2.33 | | |
| | | 7.29 | | |
| 2NOCl.SnCl$_4$.Mesitylene | Colored | 2.42 | | |
| | | 7.21 | | |
| 2NOCl.SnCl$_4$.Hexamethylbenzene | 3360 | 2.49 | | |
| 2NOCl.TiCl$_4$.2 Toluene | Colored | 2.52 | 20.9 | |
| | | 7.41 | 135.2 | |
| 2NOCl.TiCl$_4$.p-Xylene | Colored | 2.38 | | |
| | | 7.30 | | |
| 2NOCl.TiCl$_4$.Mesitylene | 2850 | 2.52 | 20.9, 135.2 | 2.6 × 10$^{-10}$ |
| | | 7.41 | | |
| 2NOCl.TiCl$_4$.Hexamethylbenzene | 3100 | 2.50 | 17.3, 150.2 | |
| 2NOCl.TiCl$_4$.Naphthalene | Colored | | | |
| 2NOCl.ZrCl$_4$.2 Toluene | Colored | | | |
| 2NOCl.ZrCl$_4$.2 Hexamethylbenzene | Colored | 2.48 | | |
| SOCl$_2$.AlCl$_3$.Hexamethylbenzene | Colored | 2.37 | | |
| SOCl$_2$.FeCl$_3$.Hexamethylbenzene | Colored | | | 4.3 × 10$^{-10}$ |
| SOCl$_2$.FeCl$_3$.Thiophene | Colored | | | 5.3 × 10$^{-8}$ |
| SOCl$_2$.FeCl$_3$.Furan | Colored | | | 2.2 × 10$^{-9}$ |
| POCl$_3$.FeCl$_3$.Hexamethylbenzene | Colored | | | 3.0 × 10$^{-9}$ |
| POCl$_3$.FeCl$_3$.Furan | Colored | | | 1.3 × 10$^{-10}$ |

TABLE 1-continued

| Complex | Absorption (λ max Å) | Chemical Shift ($\delta^1H$, $\delta^{13}C$) | | Conductivity (ohm$^{-1}$ cm$^{-1}$) |
|---|---|---|---|---|
| NOCl.NbCl$_5$.p-Xylene | Colored | 2.57, 7.67 | | |
| NOCl.NbCl$_5$.Mesitylene | Colored | 2.52, 7.44 | | |
| NOCl.NbCl$_5$.Hexamethylbenzene | Colored | 2.49 | | |
| NOCl.TaCl$_5$.Toluene | Colored | 2.57, 7.7, 7.8 | 21.35, 133.7, 136.1, 137.0, 149.3 | |
| NOCl.TaCl$_5$.Mesitylene | Colored | 2.58, 7.57 | 21.23, 138.94, 153.44 | |
| NOCl.TaCl$_5$.Hexamethylbenzene | Colored | 2.48 | 17.46, 150.34 | Crystal Structure |
| NOF.TaCl$_5$.Hexamethylbenzene | Colored | 2.50 | 17.28, 150.30 | |
| NOCl.WCl$_6$.Hexamethylbenzene | Colored | | | |
| 2NOCl.GeF$_4$.Hexamethylbenzene | Colored | 2.5 | 16.7 | |
| 2NOF.SnCl$_4$.Hexamethylbenzene | 3360 | 2.50 | 17.3, 150.2 | |

The organometallic charge transfer complex may be prepared by admixing the inorganic chloride or fluoride RX, the Lewis acid metal halide MX$_m$ and the aromatic compound Ar.

It is convenient to admix the above starting materials in a suitable inert solvent, for example, a non-aromatic non-polar organic solvent, such as cyclohexane; a chlorinated hydrocarbon solvent, for example, carbon tetrachloride, chloroform, methylene chloride, or liquid sulfur dioxide. It is particularly convenient to admix first the inorganic halide and the metal halide in a solvent thereby forming a precursor a(R).MX$_{(a+m)}$ (i.e. aRX.MX$_m$) and then add to the precursor the aromatic compound in an inert solvent, preferably the same solvent as used for preparing the precursor. Thereafter the solvent may be removed, for example, by filtration, and the solid complex may be dried under reduced pressure.

The formation of a charge transfer complex has been verified by various measurements including ultraviolet-visible spectroscopy, proton and carbon magnetic resonance spectroscopy, weight measurements, crystal structure, conductivity and electron spin resonance spectroscopy.

These complexes are in general solid and intensely colored.

Both proton and carbon resonance spectra of the NOCl.AlCl$_3$.benzene complex showed rapid averaging of the signals from free and complexed benzene, even at $-64°$ C. Calculations based on the chemical shifts as a function of the excess concentration of benzene indicated essentially complete complex formation with an equilibrium constant greater than 2,000. Stronger complexes are formed with methyl substituted benzenes than with benzene itself since a(NOCl).MCl$_m$ precursors derived from BCl$_3$, SnCl$_4$, TiCl$_4$, ZrCl$_4$ and AsCl$_3$ form complexes with p-xylene or toluene, but not with benzene. From the above observations an approximate order of ability to form these charge-transfer complexes is: 2(NOCl).SnCl$_4$ < 2(NOCl).TiCl$_4$, 2(NOCl).ZrCl$_4$, NOCl.BCl$_3$, NOCl.AsCl$_3$ < NOF.BF$_3$ < NOF.AsF$_5$ < NOCl.AlCl$_3$, NOCl.FeCl$_3$, NOCl.SbCl$_5$.

Proton magnetic resonance spectroscopy of these complexes shows a shift in the direction of deshielding. For example, with strongly complexing hexamethylbenzene there is a shift from 2.15 p.p.m. for the methyl proton in the free aromatic to 2.48±0.01 for that in the complexes with NOCl.AlCl$_3$ (or NOAlCl$_4$), (NO)$_2$SnCl$_6$ (or 2(NOCl).SnCl$_4$), (NO)$_2$TiCl$_6$ (or 2(NOCl).TiCl$_4$) and (NO)$_2$.ZrCl$_6$ (or 2(NOCl).ZrCl$_4$). With the complexes of mesitylene the proton shifts are from 2.23 (methyl proton) and 6.81 (ring proton) for the free aromatic to 2.58 and 7.58 for the strongly complexing NOAlCl$_4$ (or NOCl.AlCl$_3$), but only 2.47 and 7.33 for the weaker complexes with (NO)$_2$SnCl$_6$ (or 2(NOCl).SnCl$_4$ and (NO)$_2$.TiCl$_6$ (or 2(NOCl).TiCl$_4$).

Ultraviolet-visible spectroscopy shows a shift of the absorption band of the aromatic compounds to longer wavelength when they are in the charge transfer complex. For example, an absorption band of benzene shifts from 2680 Å for the free compound to 3350 Å for a complex with NOCl.AlCl$_3$ and an absorption band of mesitylene shifts from 2820 Å for the free compound to 3430 Å for a complex with NOCl.AlCl$_3$. It is interesting that although it may be said that stronger charge transfer complexes are formed between NOCl.AlCl$_3$ and aromatics than with tetracyanoethylene as an acceptor based on the equilibrium constants obtained from proton and carbon magnetic resonance spectroscopy, the shift of the charge transfer band to longer wavelength is less with the NOCl.AlCl$_3$ complexes than the tetracyanoethylene complexes. Tetracyanoethylene, with benzene, shifts to 3840 Å and with mesitylene to 4610 Å.

The complexes of the invention are relatively stable. It has been noticed that the stronger complexes do not discolor in acetone while the weaker ones become colorless, indicating that they decompose.

The organometallic charge transfer complexes of the invention have a certain degree of conductivity. For example, the conductivity of a single crystal of NOCl.SbCl$_5$.hexamethylbenzene was found to be $2.3 \times 10^{-3}$ ohm$^{-1}$ cm$^{-1}$ at 25° C. Although a single sharp proton resonance line is observed for this compound in solution, an E.S.R. signal is observed in the solid at 25° and $-196°$ C. The observed g value of 2.0028 is essentially that of a free electron. The line width is the same at both temperatures but the intensity is much greater at low temperature with a suggestion of some hyperfine structure. These results suggest that additional electron delocalization occurs in the solid and that the conduction may occur by a metallic rather than semi-conductor mechanism. The complexes of the invention having relatively small degree of conductivity may be used as semi-conductors, and some may be used as dyes or inks. All complexes are intensely colored, accordingly it is expected that these complexes absorb light over a wide visible spectrum, thus may be used as photovoltaic materials.

Crystals of NOCl.SbCl$_5$·hexamethylbenzene are orthorhombic in space group Pbcm with a=8.2375(5), b=19.466(2), c=12.406(1) Å and Z=4. The NO moiety is disordered with the oxygen in one of two equivalent positions. The nitrogen is placed nearly symmetrically at an average separation of only 2.35 Å from the six aromatic carbon atoms. The most obvious pathway for electron delocalization is along the line of NO groups and the associated aromatic rings.

The charge transfer complexes of the present invention may be made with relatively cheap materials including abundantly available aromatic compounds and ordinary Lewis acids, thus eliminating expensive materials particularly prepared for the purpose, such as tetracyanoethylene and tetracyanoquinodimethane. It will be, also appreciated that the process of the manufacture is also simple, thus reducing the manufacturing costs.

The following are examples of the preparation of organometallic charge transfer complexes according to the invention.

EXAMPLE 1

0.5 gram of $AlCl_3$ was dissolved in 3 c.c. of NOCl and all volatile materials were removed under vacuum to give $NOAlCl_4$. 0.608 g of hexamethylbenzene and 3 c.c. of liquid $SO_2$ were added to the precursor and after mixing all volatile materials were removed under vacuum to leave a black charge transfer complex $NOCl\cdot AlCl_3\cdot$hexamethylbenzene.

EXAMPLE 2

To 1 g of $SbCl_3$ dissolved in 3 c.c. of $CCl_4$ was added 3 c.c. of $SOCl_2$. One c.c. of thiophene dissolved in 3 c.c. of $CCl_4$ is slowly added with vigorous stirring. The black solid is filtered, washed with a little $CCl_4$ and dried under vacuum to obtain a charge transfer complex $SOCl_2\cdot SbCl_3\cdot$thiophene.

EXAMPLE 3

0.34 gram of $AsF_5$ and 0.1 gram of NOF were dissolved in 1.5 gram of $SO_2$ and all volatiles were removed under vacuum to give 0.4 gram of $NOAsF_6$. 0.30 gram of hexamethylbenzene and 2 c.c. of liquid $SO_2$ were added to the precursor and after mixing all volatile materials were removed under vacuum to leave a black charge transfer complex $NOF\text{-}AsF_5\text{-}$hexamethylbenzene. This material has absorption maxima at 3,340 and 2,700 Å. Its resistivity is $4.34 \times 10^6$ ohm cm. Its structure is shown to be $NO\text{-}AsF_6\text{-}$hexamethylbenzene by X-ray diffraction from a single crystal.

What is claimed is:

1. An organometallic ternary charge transfer complex of formula (I)

$$a(RX)\cdot MX_m\cdot b(Ar) \qquad (I)$$

wherein $MX_m$ is a Lewis acid metal chloride or fluoride,

RX is an inorganic chloride or fluoride which contains at least one oxygen and/or sulfur atom and is capable of forming a complex salt $a(R)\cdot MX_{(a+m)}$ with the Lewis acid $MX_m$, Ar is an aromatic compound with the proviso that unsubstituted benzene is excluded when $MCl_m$ is $BCl_3$, $BF_3$, $SnCl_4$, $TiCl_4$, $ZrCl_4$ or $AsCl_3$, m is an integer representing the valency of the metal M, a is an integer selected such that the sum of a and m does not exceed the coordination number of the metal M of the given valency, b is 0.5, 1 or 2.

2. A charge transfer complex of claim 1, wherein the inorganic chloride RCl is NOCl, $SOCl_2$ or NOF.

3. A charge transfer complex of claim 2, wherein the metal halide $MX_m$ is selected from the group consisting of $BCl_3$, $BF_3$, $AlCl_3$, $GaCl_3$, $TlCl_3$, $AsCl_3$, $AsF_5$, $SbCl_5$, $FeCl_3$, $SnCl_4$, $TiCl_4$, $ZrCl_4$, $NbCl_5$, $TaCl_5$ and $WCl_6$.

4. A charge transfer complex of claim 2, wherein the metal chloride $MCl_m$ is $AlCl_3$, $SbCl_3$, $SbCl_5$ or $FeCl_3$.

5. A charge transfer complex of claim 2, wherein the aromatic compound Ar is selected from the group consisting of naphthalene, anthracene, polycondensed aromatic hydrocarbons, thiophene, furan, polystyrene, N-substituted pyrroles, porphyrins and benzene which is unsubstituted or substituted with lower alkyl, halogen, diloweralkylamino, oxo or lower alkoxy.

6. A charge transfer complex of claim 2, wherein the aromatic compound Ar is naphthalene, anthracene, thiophene, furan, toluene, xylene, mesitylene, hexamethylbenzene, N,N-dimethylaniline or bromobenzene.

7. A charge transfer complex of claim 2, wherein the aromatic compound Ar is benzene which is substituted with 1 to 6 methyl groups.

8. A charge transfer complex of claim 2, wherein a is 1 or 2, and b is equal to a.

9. A charge transfer complex of claim 6, wherein the metal chloride $MCl_m$ is $AlCl_3$, $FeCl_3$ or $SbCl_5$.

10. A charge transfer complex of claim 8, wherein the inorganic chloride is NOCl, the metal chloride is $AlCl_3$, $FeCl_3$ or $SbCl_5$, and the aromatic compound is hexamethylbenzene, mesitylene, thiophene or furan.

11. A method for producing the ternary charge transfer complex of formula (II) as defined in claim 1, which method comprises admixing a Lewis acid metal halide $MX_m$, an aromatic compound Ar and an inorganic chloride RCl which contains at least one oxygen atom and/or sulfur atom and is capable of forming a complex salt $a(R)\cdot MX_{(a+m)}$ with the Lewis acid.

12. A method of claim 11, wherein the ingredients are admixed in liquid sulfur dioxide or a non-aromatic non-polar organic solvent.

13. A method of claim 11, wherein the inorganic halide and the Lewis acid metal halide are first admixed to form a precursor of the formula $a(R)\cdot MX_{(a+m)}$, and thereafter the aromatic compound is added to the precursor as a solution in a solvent.

* * * * *